United States Patent [19]

Henrick

[11] 4,021,461

[45] May 3, 1977

[54] ALIPHATIC HYDROCARBON 2,4-DIENOIC ACIDS, ESTERS AND DERIVATIVES THEREOF

[75] Inventor: Clive A. Henrick, Palo Alto, Calif.

[73] Assignee: Zoecon Corporation, Palo Alto, Calif.

[22] Filed: June 23, 1972

[21] Appl. No.: 265,922

Related U.S. Application Data

[63] Continuation-in-part of Ser. No. 201,102, Nov. 22, 1971, abandoned, which is a continuation-in-part of Ser. No. 111,673, Feb. 1, 1971, abandoned, Ser. No. 111,701, Feb. 1, 1971, abandoned, Ser. No. 111,767, Feb. 1, 1971, abandoned, and Ser. No. 187,898, Oct. 8, 1971, Pat. No. 3,752,843.

[52] U.S. Cl. .................. 260/410.9 N; 260/399; 260/408; 260/410; 260/410.5; 260/410.6; 260/410.9 R; 260/413; 260/414; 260/455 R; 260/502.6; 424/301; 260/312; 260/318

[51] Int. Cl.² .................. C07C 69/61; C07C 69/52; A01N 9/24

[58] Field of Search ............ 260/410.9 R, 413, 408, 260/405, 414

[56] References Cited

UNITED STATES PATENTS

| | | | |
|---|---|---|---|
| 2,951,853 | 9/1960 | Matsui | 260/347.5 |
| 3,651,104 | 3/1972 | Siddall | 260/410.9 R |
| 3,657,291 | 4/1972 | Jarolim et al. | 260/408 |
| 3,671,558 | 1/1972 | Siddall et al. | 260/410.9 R |
| 3,697,565 | 10/1972 | Siddall | 260/408 |
| 3,712,922 | 1/1973 | Henrick et al. | 260/410.9 R |
| 3,716,565 | 2/1973 | Henrick et al. | 260/410.9 R |

FOREIGN PATENTS OR APPLICATIONS

| | | |
|---|---|---|
| 2,038,958 | 2/1971 | Germany |
| 2,115,673 | 10/1971 | Germany |

OTHER PUBLICATIONS

Wiley et al., J. Am. Chem. Soc., vol. 79, pp. 2266–2271, (1957).

*Primary Examiner*—Donald G. Daus
*Assistant Examiner*—Diana G. Rivers
*Attorney, Agent, or Firm*—Donald W. Erickson

[57] ABSTRACT

Novel aliphatic hydrocarbon di-olefinic acids, esters, thiolesters, and derivatives thereof, intermediates therefor, syntheses thereof and the control of insects.

33 Claims, No Drawings

ALIPHATIC HYDROCARBON 2,4-DIENOIC ACIDS, ESTERS AND DERIVATIVES THEREOF

This is a continuation-in-part of application Ser. No. 201,102, filed Nov. 22, 1971, now abandoned, which is a continuation-in-part of application Ser. Nos. 111,673, filed Feb. 1, 1971, now abandoned, Ser. No. 111,701, filed Feb. 1, 1971, now abandoned, Ser. No. 111,767, filed Feb. 1, 1971, now abandoned, and Ser. No. 187,898, filed Oct. 8, 1971, now U.S. Pat. No. 3,752,843, the disclosures of which are incorporated by reference.

This invention relates to novel alphatic di-olefinic compounds, intermediates therefor, synthesis thereof and the control of insects. More particularly, the novel di-olefinic compounds of the present invention are represented by the following formula (A):

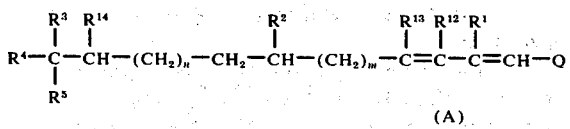

(A)

wherein,
each of $m$ and $n$ is zero or the positive integer one, two or three;
each of $R^1$ and $R^2$ is lower alkyl;
$R^4$ is akyl;
each of $R^3$, $R^5$, $R^{12}$, $R^{13}$ and $R^{14}$ is hydrogen or lower alkyl; and Q is one of the groups:

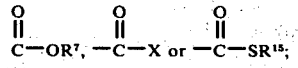

in which,
X is bromo, chloro or fluoro,
$R^7$ is hydrogen, lower alkyl, lower alkenyl, lower alkynyl, cycloalkyl, aryl, aralkyl, lower alkylthiaalkyl, lower alkoxyalkyl, halogen substituted lower alkyl, heterocyclo, or a metal cation; and
$R^{15}$ is hydrogen, lower alkyl, lower alkenyl, lower akynyl, cycloalkyl, aryl or aralkyl;

The compounds of formula A are useful for the control of insects. The utility of these compounds as insect control agents is believed to be attributable to their juvenile hormone activity. They are preferably applied to the immature insect, namely — during the embryo, larvae or pupae stage in view of their effect on metamorphosis and otherwise cause abnormal development leading to death or inability to reproduce. These compounds are effective control agents for Hemipteran such as Lygaeidae, Miridae and Pyrrhocoridae; Lepidopteran such as Pyralidae, Noctridae and Gelechiidae; Colepteran such as Tenebrionidae, Crysomelidae and Dermestidae; Dipteran such as mosquitos, flies, Homopteran such as aphids and other insects. The compounds can be applied at low dosage levels of the order of 0.001 μg. to 25.0 μg. per insect. Suitable carrier substances include liquid or solid carriers, such as water, acetone, xylene, mineral or vegetable oils, talc, vermiculite, natural and synthetic resins and silica. Treatment of insects in accordance with the present invention is accomplished by spraying, dusting or exposing the insects to the vapor of the compounds of formula A. Generally, a concentration of less than 25% of the active compound is employed. The formulations can include insect attractants, emulsifying agents or wetting agents to assist in the application and effectiveness of the active ingredient. In the application of the compounds, there is generally employed a mixture of the C-2,3 trans and cis isomers.

In the description hereinafter, each of Q, $R^1$-$R^5$, $R^7$-$R^9$, $R^{12}$-$R^{15}$, X, $m$ and $n$ is as defined hereinabove unless otherwise specified.

In one embodiment of the present invention, there is provided acids and esters included within formula A above represented by the following formula (B):

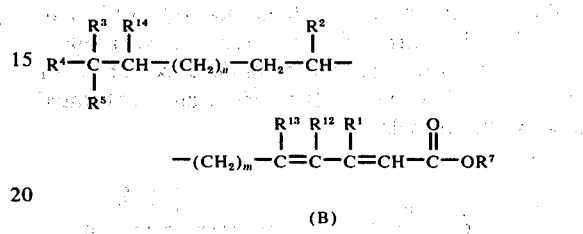

(B)

One synthesis of esters of formula B can be outlined as follows:

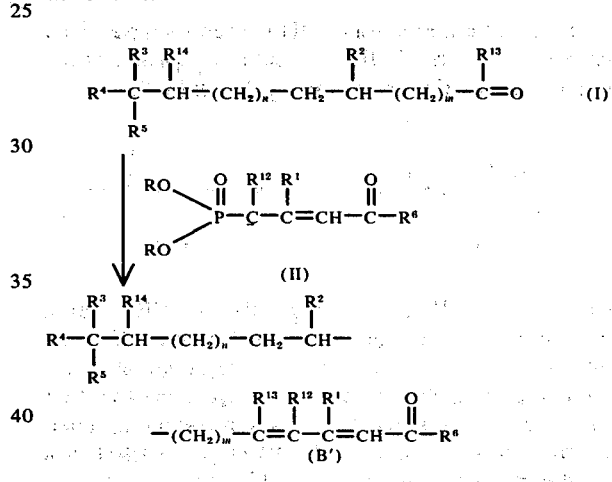

In the above formulas, R is lower alkyl, cycloalkyl or phenyl and $R^6$ is lower alkoxy, cycloalkoxy or aralkoxy.

In the above synthesis, an aldehyde ($R^{13}$ is hydrogen) or ketone ($R^{13}$ is lower alkyl) of formula I is reacted with a carbanion of formula II to yield an ester of formula B'.

The carbanion (II) is generated by treatment of the corresponding phosphonate with a base such as an alkali hydroxide, alkali hydride or alkali alkoxide, e.g. NaOH, NaH, sodium ethoxide or sodium methoxide, in an organic solvent inert to the reaction such as hydrocarbon, ether or dialkylsufloxide solvent e.g. benzene, toluene, dimethylformamide or tetrahydrofuran. The reaction is generally conducted at a temperature of from about −20° C to room temperature or above. The reaction of the carbanion with the carbonyl (1) is generally conducted at temperature of about 0° C to room temperature or above. The phosphonates can be prepared as described by Pattenden and Weedon, J. Chem. Soc. (C), 1984 and 1997 (1968), Stilz and Pommer, U.S. Pat. Nos. 3,163,669 and 3,177,226 and Corey et al., Tetrahedron Letters No. 2,1821 (1971).

A second synthesis of esters of formula B' is outlined as follows:

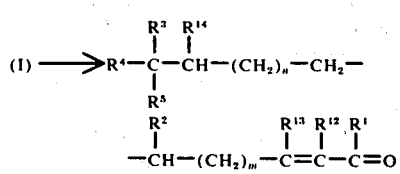

In the second synthesis outlined above of I to III to B', a carbonyl of formula I is reacted with a carbanion of formula IIA using the conditions described above or with an ylid of formula IIB to yield an unsaturated ketone of the formula III

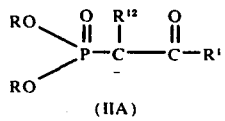 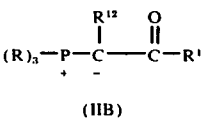

(IIA)    (IIB)

The unsaturated ketone (III) is then reacted with a carbanion of formula IIC to yield a compound of formula B' or Wittig reaction using the ylid (IID).

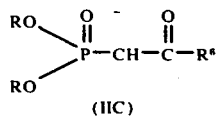 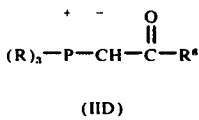

(IIC)    (IID)

Conversion of III into B' using carbanion (IIC) can be done using the same conditions as for conversion of I into III: Wittig reactions are generally done at higher temperatures such as from room temperature to reflux. The ylids are prepared from the corresponding phosphonium bromide or chloride by treatment with a base substance such as an alkali metal hydride, alkali metal hydroxide or alkali metal carbonate in an organic solvent, such as toluene, benzene, or tetrahydrofuran, or water or aqueous organic solvent depending upon the particular base. The Wittig reageants can be prepared as described in U.S. Pat. No. 3,193,565.

A synthesis for esters of formula B' which is applicable when each of $R^{12}$ and $R^{13}$ is hydrogen is outlined as follows:

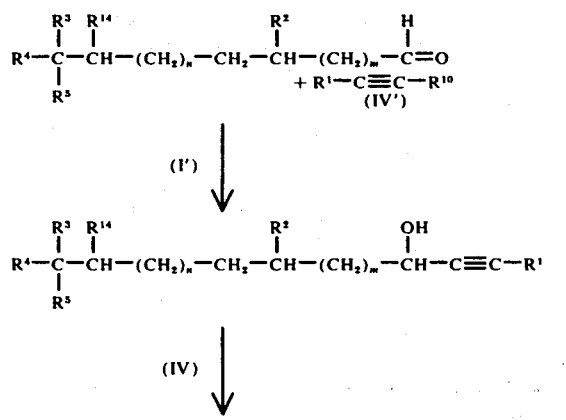

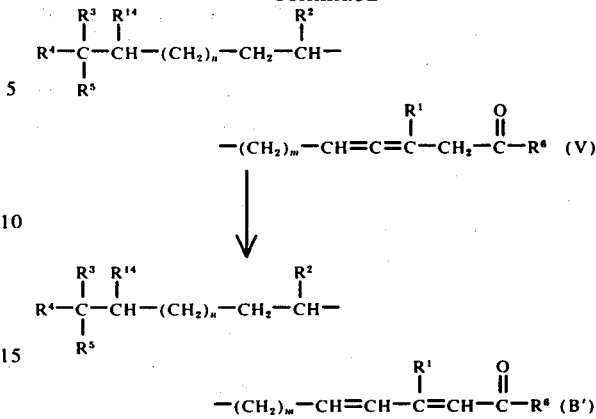

$R^{10}$ is a metal such as lithium, sodium, potassium or magnesium.

In the third synthesis outlined above, an aldehyde of formula I' is reacted with an alkyne of formula IV' to produce the alkynyl alcohol of formula IV. A compound of formula IV is then reacted with an orthoester in the presence of weak acid catalyst to yield an allenic ester of formula V which is rearranged to 2,4-diunsaturation by treatment with base such as described in copending application Ser. No. 111,768, filed Feb. 1, 1971, now U.S. Pat. No. 3,716,565. Preparation of alkynyl alcohols is described by Kimel et al, J. Org. Chem. 22 1611 (1957). The conversion of alkynyl alcohols to allenic esters is described by Crandall et al, Chem. Comm., 1411 (1970).

Another synthesis of acids and esters of formula B involves base catalyzed condensation wherein an aldehyde such as an aldehyde of formula I' is reacted with an ester of the formula

in the presence of an inorganic or organic base. Suitable base include sodium amide, potassium amide, potassium hydroxide, and the like as described in U.S. Pat. Nos. 2,662,914 and 2,951,853. The novel acids produced by this method are then converted into the desired ester using conventional methods such as preparation of the acid halide followed by reaction with an alcohol.

The esters of formula B and B' are converted into the corresponding acid by hydrolysis with base such as potassium carbonate, sodium carbonate, sodium hydroxide, and the like in organic solvent such as methanol or ethanol. Other esters of the present invention can be prepared by transesterification or conversion of the acid into the acid halide by treatment with thionyl chloride, oxalyl chloride, phosphorous pentabromide or the like, and then reacting the acid halide with the alcohol corresponding to the ester moiety desired. Acyl fluorides (X is fluoro) are prepared by reacting the acyl bromide or acyl chloride with one mole anhydrous hydrogen fluoride under dry conditions and at low temperature such as about −5° C for a few minutes.

In a second embodiment of the novel compounds of the present invention, there is provided thio-acids and thiol esters of formula A. Thio-acids and thiol esters

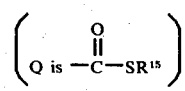

can be prepared from the respective acid halide using hydrogen sulfide to prepare the thio-acid and a thiol $R^{15}$—SH in pyridine or a mercaptide to prepare the thiol ester. Thiol esters can be prepared by alkylation of the sodium salt of a thio-acid of the present invention also. See U.S. Pat. Nos. 3,567,747 and 3,505,366.

Synthesis of aldehydes and ketones of formula I can be accomplished using methods known in the art. Many of the carbonyl precursours of formula I are commercially available. The aldehydes of formula I wherein each of $R^3$ and $R^5$ is lower alkyl can be prepared by oxidation of the corresponding primary alcohol using chromic acid, manganese dioxide or the like as described in copending application Ser. No. 6291, filed Jan. 27, 1970, now U.S. Pat. No. 3,706,804, the disclosure of which is incorporated by reference. The primary alcohols are described in copending application Ser. No. 854,778, filed Sep. 2, 1969, now U.S. Pat. No. 3,649,590, and 879,620, filed Nov. 24, 1969, now abandoned, the disclosures of which are incorporated by reference. The aldehydes of formula I wherein either $R^3$ or $R^5$ is hydrogen can be prepared by controlled oxidation, as described above, of the corresponding alcohol. In the case of unsaturated primary alcohols, hydrogenation of any unsaturated bond(s) using palladium on carbon or the like can be done either prior to or after conversion of the alcohol to the aldehyde.

Compounds of formula I wherein m is one, two or three can be prepared utilizing carbonyl precursors as outlined below:

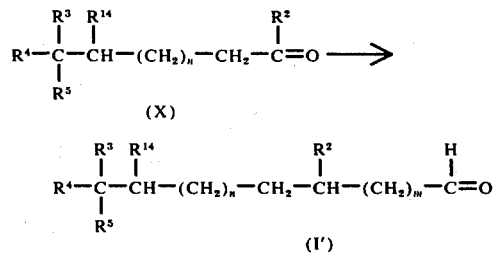

In the practice of the above synthesis, a carbonyl of formula X is reacted with a lower alkoxymethyltriphenylphosphonium halide such as methoxymethyltriphenylphosphoniumm chloride in the presence of alkyllithium, aryl lithium or the like followed by treatment with acid to afford an aldehyde of formula I' wherein m is zero. Suitable conditions for this reaction are described by Nelson, U.S. Pat. No. 3,562,336. By repeating this reaction using the thus-prepared aldehyde as the starting material, an aldehyde of formula I' wherein m is one is prepared. Aldehydes of formula I' wherein m is two and three are prepared by simply repeating the foregoing reaction using the appropriate precursor of formula I' wherein m is one and two, respectively.

Compounds of formula I wherein $R^{13}$ is lower alkyl can be prepared by reaction of an aldehyde of formula I' with a Grignard $R^{13}$ MgX ($R^{13} \neq H$) following by oxidation.

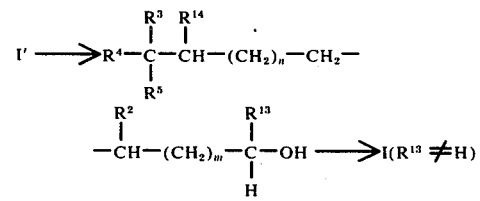

Ketones of formula X can be prepared according to methods described in the literature. A general procedure for compounds of formula X, in which n is one, two or three, can be outlined as follows ($\phi$ is phenyl and $n'$ is two, three or four):

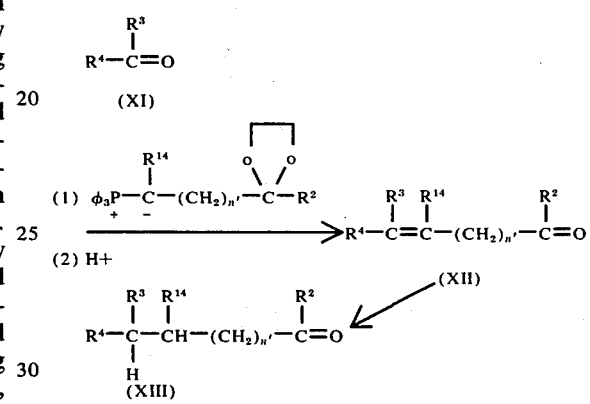

In the above process, a ketone of formula XI is reacted with the phosphonium ylid in the presence of alkyl lithuim to phenyl lithuim to yield the ketal of XII, which is treated with aqueous acid to yield the carbonyl XII. The olefinic carbonyl (XII) is hydrogenated using palladium or other hydrogenation catalyst to yield (XIII). The ylid is prepared by the reaction of triphenylphosphine with a chloride of the formula:

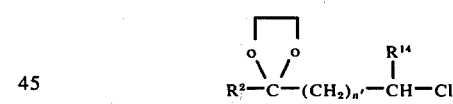

Suitable procedures for the preparation of the ylid and Wittig reactions are described by A W Johnson, "Ylid Chemistry", Academic Press Inc. New York (1966). U.S. Pat. Nos. 3,078,256 and 3,130,219, Canadian Pat. No. 834,191, and Chem. Comm. 733. July 1969.

A general method for the preparation of precursors of the formula I and XIII, particularly wherein n is zero or one, is the reaction of an allyl alcohol with an enol ether followed by hydrogentation. See U.S. Pat. Nos. 3,381,039, 3,428,694 and 3,493,619. A good review of the preparation of aldehydes is provided by Sisti et al., *J. Org. Chem.* 27 279 (1962); Piacenti, *Gazz. Chem. Ital.* 92, 225 (1962); Burgstachler. *J. Org. Chem.* 28 (10), 2918 (1963); Johnson et al., *J. Chem Soc.*, 520 (1964); Naves, *Chim. Ind.* (Paris), 94 (3), 223 (1965); Carnduff, *Quart Rev.* (London) 20 (2), 169 (1966); and Mahadevan et al., *Lipd l* (13), 183 (1966).

Examples of carbonyl compounds included within formulas I and I' useful for the preparation of compounds of the invention are the following.

dihydrocitronellal
3,7-dimethylnonan-1-al
3-methyloctan-1-al
3-methyl-7-ethylnonan-1-al
3-ethyl-7-methylnonan-1-al
3,7-diethylnonan-1-al
3,7,7-trimethyloctan-1-al
3,7,7-trimethylnonan-1-al
3,6,7-trimethyloctan-1-al
3,6,7-trimethylnonan-1-al
3,7,8-trimethylnonan-1-al
3,7-dimethyldecan-1-al
3,7-dimethylundecan-1-al
2,4,5-trimethylhexan-1-al
2,5,5-trimethylhexan-1-al
2,4,5-trimethylheptan-1-al
2,5,5-trimethylheptan-1-al
3,5,6-trimethylheptan-1-al
3,6,6-trimethylheptan-1-al
3,5,6-trimethyloctan-1-al
3,6-dimethylheptan-1-al
3,6-dimethyloctan-1-al
2,6-dimethylheptan-1-al
2,5,6-trimethylheptan-1-al
2,6-dimethyloctan-1-al
2,6,6-trimethylheptan-1-al
2,6,6-trimethyloctan-1-al
4,7,8-trimethylnonan-1-al
4,8-dimethylnonan-1-al
4,8,8-trimethylnonan-1-al
4,8-dimethyldecan-1-al
3,8-dimethylnonan-1-al
3,8-dimethyldecan-1-al
3,7,8-trimethyldecan-1-al
4,9-dimethyldecan-1-al
3,9-dimethyldecan-1-al
2,9-dimethyldecan-1-al The term "cycloalkyl", as used herein, refers to a cyclic alkyl group of three to eight carbon atoms. The term "aralkyl" refers to a monovalent hydrocarbon group in which an aryl group is substituted for a hydrogen atom of an alkyl group, such as benzyl, xylyl, mesityl, phenylethyl, methylbenzyl, naphthylmethyl and naphthylethyl containing up to twelve carbon atoms. The term "aryl", as used herein, refers to an aromatic group of up to twelve carbon atoms. Typical aromatic groups include phenyl, naphthyl, lower alkylphenyl such as methylphenyl, ethylphenyl and t-butylphenyl isopropylphenyl, lower alkylthiophenyl such as methylthiophenyl, ethylthiophenyl and isopropylthiophenyl, lower alkoxyphenyl such as methoxyphenyl and ethoxyphenyl, halophenyl such as chlorophenyl, bromophenyl, iodophenyl and fluorophenyl, nitrophenyl, methylenedioxyphenyl, lower alkenylphenyl such as vinylphenyl and allylphenyl, phenylketones such as acetophenome, benzoic esters such as lower alkyl benzoate and benzomides such N-lower alkyl benzamide and N,N-di (lower alkyl) benzamide. In the case of substituted phenyl, the substituent such as lower alkyl, lower alkylthio, lower alkoxy, halo, lower alkenyl carbonyl, lower alkoxycarbonyl, cyano, and amido can be in one or more positions of the phenyl ring, usually in the para position. The term "heterocyclo" as used herein, refers to a heterocyclic group consisting of four or five carbon atoms and one heteroatom which is oxygen, nitrogen or sulfur such as the heterocyclics pyridine, pyran, thiophan, pyrole, furan and thiophen.

The term "alkoxyalkyl", as used herein, refers to an alkyl group substituted with one alkoxy group, e.g. methoxymethyl, 2-methoxyethyl, 4-ethoxybutyl, n-propoxyethyl and t-butoxyethyl. The term "alkenyl", as used herein, refers to an ethylenically mono- or di-unsaturated aliphatic hydrocarbon group, branched or straight chain, having a chain length of three to twelve carbon atoms e.g. allyl, 3-butenyl, 3-hexenyl and i-propenyl. Whenever any of the foregoing terms are modified by the word "lower", the chain length of the group is not more than six carbon atoms with the exception of lower alkoxyalkyl and lower alkylthiaalkyl in which event a total chain length of twelve carbon atoms is the maximum. The term "halogen substituted lower alkyl", as used herein, refers to a lower alkyl group substituted with one to three halogen atoms such as chloromethyl, fluoromethyl, 2,2,2-trifluoroethyl 2,2,2-trichloroethyl and the like. The term "lower alkynyl", as used herein, refers to a mono-acetylenically unsaturated alphatic hydrocarbon having a chain length of three to six carbon atoms.

The term "metal", as used herein, refers to lithium, sodium, potassium, calcium, strontium, copper, manganese and zinc. The term "alkyl" refers to a saturated aliphatic hydrocarbon of one to 12 carbon atoms. The term "lower alkyl" refers to an alkyl group having a chain length of one to six carbon atoms.

In addition to the compounds of the present invention having activity useful for the control of insects, the compounds of formula A have numerous other useful applications. For example, the esters of formula B of the present invention are useful lubricants and plasticizers for polymers such as SBR, polybutadiene, ethylene-propylene copolymers and polypropylene and aid in the processing and application of polymers.

The presence of an olefinic bond at position C-2 and C-4 gives rise to four isomers, each of which is embraced by the present invention. As mentioned above, a mixture of isomers is suitably employed for the control of insects such as a mixture containing the trans (2), trans (4) isomer and the cis (2), trans (4) isomer. The conditions of the syntheses described herein and the reactants can be selected so as to favor formation of one isomer such as the all trans isomer over the formation of other isomers. The selection of appropriate conditions and reactants to favor formation of one isomer over another will be apparent to those of ordinary skill in the art giving due consideration to the specific examples hereinafter. See also Pattenden and Weedon, supra and Corey et al, supra. In the specific examples hereinafter, when isomerism is not specified, it is understood to include a mixture of isomers which, if desired, can be separated using known separation methods. Hereafter, when only one designation of configuration is given, the designation refers to position C-2,3 and the configuration is taken to be trans at position C-4,5 when not otherwise specified. The use of "trans/cis" and "cis/trans" is with reference to position C-2,3 and indicates a mixture of isomers.

The following examples are provided to illustrate the practice of the present invention. Temperature is given in degrees Centigrade.

EXAMPLE 1

Sodium methoxide (from 200 mg. sodium and 12 ml. methanol) is added dropwise to a stirred solution of 1.8 g. of trans diethyl 3-ethoxycarbonyl-2-methylprop-2-enyl phosphonate (II; R = ethyl, $R^1$ = methyl and $R^6$ = ethoxy) and 1 g. of 3,7-dimethyl-1-nonanal in 50 ml. of dimethylformamide under nitrogen. The reaction mixture is left for one hour at room temperature and then water is added followed by extraction with ether. The ethereal extracts are washed with brine, dried and evaporated to yield trans/cis methyl 3,7,11-trimethyltrideca2,4-dienoate. The isomeric mixture can be chromatographed on silica or distilled for purification. The isomeric mixture is predominantly trans at C-2,3.

The foregoing procedure is repeated using ethyl 3-methoxycarbonyl-2-methylprop-2-enyl phosphonate and each of 3-methyl-7-ethylnonan-1-al,
3,7-diethylnonan-1-al
3,6,7-trimethyloctan-1-al,
3,7,8-trimethylnonan-1-al,
3-methyloctan-1-al,
3,6,7-trimethylnonan-1-al and
2,4,5-trimethylhexan-1-al to prepare
methyl 3,7-dimethyl-11-ethyltrideca-2,4-dienoate,
methyl 3-methyl-7,11-diethyltrideca-2,4-dienoate,
methyl 3,7,10,11-tetramethyldodeca-2,4-dienoate,
methyl 3,7,11,12-tetramethyltrideca-2,4-dienoate,
methyl 3,7-dimethyldodeca-2,4-dienoate,
methyl 3,7,10,11-tetramethyltrideca-2,4-dienoate and
methyl 3,6,8,9-tetramethyldeca-2,4-dienoate, respectively.

The foregoing procedure is repeated using sodium ethoxide in place of sodium methoxide to yield trans/cis ethyl 3,7,11-trimethyltrideca-2,4-dienoate.

EXAMPLE 2

To a mixtue of 250 mg. of sodium hydride in 2 ml. of tetrahydrofuran, with ice-cooling, is added 1.6 g. of trans diethyl 3-ethoxycarbonyl-2-methylprop-2-enyl phosphonate in 5 ml. of tetrahydrofuran. Temperature is allowed to rise to room temperature and after 30 minutes, 0.95 g. of 3-ethyl-7-methyl-1-nonanal is added. After about one hour at room temperature, the mixture is extracted with ether. The ethereal extracts are washed with brine, dried and evaporated to yield trans/cis ethyl 3,11-dimethyl-7-ethyl-trideca-2,4-dienoate (about 1:1 mixture of C-2,3 trans and cis isomers).

EXAMPLE 3

To 125 mg. of a 57% dispersion of sodium hydride in oil is added pentane. The pentane is removed and the sodium hydride washed several times with pentane. To the washed sodium hydride is added 582 mg. of diethyl acetylmethylphosphonate (IIA; R is ethyl, $R^1$ is methyl) in 5 ml. of tetrahydrofuran at $-10°$ under argon. After several minutes, the solution is transferred to a solution of 425 mg. of 3,7-dimethyloctan-1-al in about 4 ml. of dry tetrahydrofuran under argon over a period of about 20 minutes at room temperature. After about two hours, water is added followed by addition of ether and the layers separated. The organic layer is washed with saturated sodium chloride, dried over sodium sulfate and evaporated under reduced pressure to yield 6,10-dimethylundec-3-en-2-one.

EXAMPLE 4

32.2 Grams of sodium hydride (57% in oil) is placed in a dry, one liter, 3-neck flask (fitted with a nitrogen inlet) and washed three times (100 ml. each) with dry pentane under nitrogen, carefully decanting only the solvent each time, into a beaker of ethanol. 400 Milliliters dry tetrahydrofuran is then added, the mixture cooled to 0°, and 156.0 g. of diethyl carbethoxymethyl phosphonate is added under nitrogen. The solution is stirred for 0.5 hour after addition is complete, and then 120 g. of 6,10-dimethylundec-3-en-2-one in 250 ml. dry tetrahydrofuran is added over about 0.5 hour period at room temperature under nitrogen. The mixture is stirred overnight at 60° and then poured into saturated NaCl at 0° and extracted with ether (3 × 200 ml.), the organic layers dried (CaSO$_4$) and concentrated under reduced pressure to yield trans/cis ethyl 3,7, 11-trimethyldodeca-2,4-dienoate which can be separated into the individual C-2,3 trans and cis isomers using gas-liquid chromatography or fractional distillation.

EXAMPLE 5

A mixture of 1 g. of trans/cis methyl 3,7,11-trimethyldodeca-2,4-dienoate, 60 ml. of methanol, 0.5 g. of sodium hydroxide and 6 ml. of water is stirred at about 30° for about 56 hours. The mixture is then diluted with water, neutralized and extracted with ether. The organic phase is washed with water, dried over sodium sulfate and evaporated to yield trans/cis 3,7,11-trimethyldodeca-2,4-dienoic acid.

EXAMPLE 6

One gram of thionyl chloride is added with stirring at room temperature to 0.5 g. of trans/cis 3,7,11-trimethyldodeca-2,4-dienoic acid and the mixture heated at about 50° for 10 minutes. Excess thionyl chloride is removed by evaporation and then t-butyl alcohol (about 2 equivalents) is added and the mixture heated at about 50° for about 5 minutes. Excess t-butyl alcohol is removed by evaporation to yield trans/cis t-butyl 3,7,11-trimethyldodeca-2,4-dienoate which is purified by chromatography.

EXAMPLE 7

Similarly, by using other alcohols such as s-butyl alcohol, n-propanol, i-butyl alcohol, cyclohexyl alcohol, benzyl alcohol, phenol, n-pentanol, n-hexyl alcohol or i-propanol in the procedure of Example 6 in place of t-butyl alcohol, the corresponding esters are obtained, i.e.

s-butyl 3,7,11-trimethyldodeca-2,4-dienoate,
n-propyl 3,7,11-trimethyldodeca-2,4-dienoate,
i-butyl 3,7,11-trimethyldodeca-2,4-dienoate,
cyclohexyl 3,7,11-trimethyldodeca-2,4-dienoate,
benzyl 3,7,11-trimethyldodeca-2,4,-dienoate,
phenyl 3,7,11-trimethyldodeca-2,4,-dienoate,
n-pentyl 3,7,11-trimethyldodeca-2,4-dienoate,
n-hexyl 3,7,11-trimethyldodeca-2,4-dienoate, and
i-propyl 3,7,11-trimethyldodeca 2,4-dienoate.

EXAMPLE 8

To 1.6 g. of sodium hydride (57% in oil dispersion) in a 500 ml., 3-neck flask, fitted with a nitrogen inlet, is added 25 to 50 ml. of dry hexane or pentane and the mixture swirled under nitrogen. The NaH is allowed to settle and the solvent carefully decanted into a beaker containing ethanol. This rinsing process is repeated twice and 100 ml. dry tetrahydrofuran is added via syringe or pipet. Mixture is cooled in an ice-bath and 9.0 g. triethyl phosphonoacetate (dried over molecular sieves) is added via addition funnel over a 10 minute period. Stir an additional one-half hour. The solution of the above anion is transferred via syringe to a 125 ml. addition funnel (with pressure equalizing arm) and is added over about 1 hour to 6.73 g. of 6,10-dimethyldodec-3-en-2-one at room temperature with stirring. The homogeneous solution is then refluxed overnight (18–24 hours). The mixture is then poured into saturated sodium chloride at 0° and extracted with ether. The organic phase is dried and concentrated under reduced pressure to yield trans/cis ethyl 3,7,11-trimethyltrideca-2,4-dienoate which can be purified by chromatography or distillation.

EXAMPLE 9

41 Grams of 3,7-dimethyloctan-1-al and 80 g. of recrystallized (ethyl acetate) triphenylphosphinacetylmethylene [Ramirez et al., *J. Org. Chem.* 22, 41 (1957)] are refluxed in one liter of dry toluene for 18 hours, under nitrogen. Most of the solvent is removed in vacuo, 500 ml. pentane is added and the mixture filtered. The flask and the triphenylphosphine oxide filter cake are washed several times with pentane. The filtrate is concentrated in vacuo to yield 6,10-dimethylundec-3-en-2-one.

By use of the foregoing Wittig reaction, other aldehydes of formula I are converted into the corresponding mono unsaturated ketones of formula III.

EXAMPLE 10

One gram of triphenylphosphineacetylmethylene and 425 mg. of 3,7-dimethylnonan-1-al are dissolved in 10 ml. toluene and refluxed under nitrogen overnight. The toluene is distilled off and the formed triphenylphosphine oxide crystallized by addition of pentane. Filtration and evaporation of the pentane gives a residue, which is further purified by preparative, thin-layer chromatography, with the plate eluted with 15% ethyl acetate:hexane. Removal of the UV active band gives 6,10-dimethyldodec-3-en-2-one.

EXAMPLE 11

To a mixture of one g. of 3,7-dimethyl-1-octanal and 1.5 g. of phosphonate (II; R is ethyl, $R^1$ is methyl, $R^6$ is ethoxy) and 50 ml. of dimethylformamide, under nitrogen, is slowly added sodium ethoxide (prepared from 200 mg. of sodium and 12 ml. of ethanol). The mixture is allowed to stand at room temperature for one hour and then is worked up with ether. The ethereal extracts are dried, concentrated and then chromatographed on silica plates eluting with hexane/ether (5% ether) to yield ethyl 3,7,11-trimethyldodeca2,4-dienoate which is predominantly trans at position C-2,3.

EXAMPLE 12

Following the procedure of Example 2 or 11 each of the aldehydes under column I is reacted with the carbanion of diethyl 3-ethoxycarbonyl-2-methylprop-2-enyl phosphonate to produce the corresponding ethyl esters under column II.

I 3,7-dimethyloctan-1-al
3,7-dimethylnonan-1-al
3-ethyl-7-methylnonan-1-al
3,6-dimethylheptan-1-al
2,5-dimethylhexan-1-al
2,5-dimethylheptan-1-al
4,8-dimethylnonan-1-al
4,9-dimethyldecan-1-al
3,9-dimethyldecan-1-al

II ethyl 3,7,11-trimethyldodeca-2,4-dienoate
ethyl 3,7,11-trimethyltrideca-2,4-dienoate
ethyl 3,11-dimethyl-7-ethyltrideca-2,4-dienoate
ethyl 3,7,10-trimethylundeca-2,4-dienoate
ethyl 3,6,9-trimethyldeca-2,4-dienoate
ethyl 3,6,9-trimethylundeca-2,4-dienoate
ethyl 3,8,12-trimethyltrideca-2,4-dienoate
ethyl 3,8,13-trimethyltetradeca-2,4-dienoate
ethyl 3,7,13-trimethyltetradeca-2,4-dienoate

EXAMPLE 13

Each of the esters under column II is hydrolyzed using the procedure of Example 5 or by refluxing for about 20 hours to produce the corresponding free acid under column III.

III 3,7,11-trimethyldodeca-2,4-dienoic acid
3,7,11-trimethyltrideca-2,4-dienoic acid
3,11-dimethyl-7-ethyltrideca-2,4-dienoic acid
3,7,10-trimethylundeca-2,4-dienoic acid
3,6,9-trimethyldeca-2,4-dienoic acid
3,6,9-trimethylundeca-2,4-dienoic acid
3,8,12-trimethyltrideca-2,4-dienoic acid
3,8,13-trimethyltetradeca-2,4-dienoic acid
3,7,13-trimethyltetradeca-2,4-dienoic acid

EXAMPLE 14

Each of the aldehydes under column I is used as the aldehyde starting material in the procedure of Example 3, 9 or 10 to produce the corresponding ketone under column IV.

IV 6,10-dimethylundec-3-en-2-one
6,10-dimethyldodec-3-en-2-one
6-ethyl-10-methyldodec-3-en-2-one
6,9-dimethyldec-3-en-2-one
5,8-dimethylnon-3-en-2-one
5,8-dimethyldec-3-en-2-one
7,11-dimethyldodec-3-en-2-one
7,12-dimethyltridec-3-en-2-one
6,12-dimethyltridec-3-en-2-one

EXAMPLE 15

Each of the ketones under column IV is converted into the corresponding methyl ester under column V using the procedure of Example 4 or 8.

V methyl 3,7,11-trimethyldodeca-2,4-dienoate
methyl 3,7,11-trimethyltrideca-2,4-dienoate
methyl 3,11-dimethyl-7-ethyltrideca-2,4-dienoate
methyl 3,7,10-trimethylundeca-2,4-dienoate
methyl 3,6,9-trimethyldeca-2,4-dienoate
methyl 3,6,9-trimethylundeca-2,4-dienoate
methyl 3,8,12-trimethyltrideca-2,4-dienoate
methyl 3,8,13-trimethyltetradeca-2,4-dienoate
methyl 3,7,13-trimethyltetradeca-2,4-dienoate Each of the methyl esters under column V is hydrolyzed to the free acid using the procedure of Example 5 or by refluxing for several hours.

EXAMPLE 16

The carbanion of diethyl 3-isopropoxycarbonyl-2-methylprop-2-enyl phosphonate is reacted with each of the aldehydes under column I to prepare the respective esters under column VI following the procedure of Example 1, 2 or 11.

VI isopropyl 3,7,11-trimethyldodeca-2,4-dienoate
isopropyl 3,7,11-trimethyltrideca-2,4-dienoate
isopropyl 7-ethyl-3,11-dimethyltrideca-2,4-dienoate
isopropyl 3,7,10-trimethylundeca-2,4-dienoate
isopropyl 3,6,9-trimethyldeca-2,4-dienoate
isopropyl 3,6,9-trimethylundeca-2,4-dienoate
isopropyl 3,8,12-trimethyltrideca-2,4-dienoate
isopropyl 3,8,13-trimethyltetradeca-2,4-dienoate
isopropyl 3,7,13-trimethyltetradeca-2,4-dienoate

EXAMPLE 17

One gram of 3,7,11-trimethyltrideca-2,4-dienoic acid in 30 ml. of benzene and one mole of sodium hydride is stirred about 2 hours and then a slight excess of oxalyl chloride is added at about 0° and stirred for 1 hour. The product is worked up by removal of solvent in vacuo and extraction with pentane to yield 3,7,11-trimethyltrideca2,4-dienoyl chloride.

Using the foregoing process, there is prepared 3,7,11-trimethyldodeca-2,4-dienoyl chloride
3,11-dimethyl-7-ethyltrideca-2,4-dienoyl chloride
3,7,10-trimethylundeca-2,4-dienoyl chloride
3,6,9-trimethyldeca-2,4-dienoyl chloride
3,6,9-trimethylundeca-2,4-dienoyl chloride
3,8,12-trimethyltrideca-2,4-dienoyl chloride
3,8,13-trimethyltetradeca-2,4-dienoyl chloride
3,7,13-trimethyltetradeca-2,4-dienyyl chloride

EXAMPLE 18

Following the procedure of either Example 1, 2 or 11, each of the aldehydes under column VII is converted into the respective ester under column VIII.

VII 3,7,7-trimethyloctan-1-al
3,7,7-trimethylnonan-1-al
3,6,6-trimethylheptan-1-al
3,8,8-trimethylnonan-1-al
4,8,8-trimethylnonan-1-al

VIII ethyl 3,7,11,11-tetramethyldodeca-2,4-dienoate
ethyl 3,7,11,11-tetramethyltrideca-2,4-dienoate
ethyl 3,7,10,10-tetramethylundeca-2,4-dienoate
ethyl 3,7,12,12-tetramethyltrideca-2,4-dienoate
ethyl 3,8,12,12-tetramethyltrideca-2,4-dienoate

EXAMPLE 19

The aldehydes under column VII are used as the starting material in the process of Example 3, 9 or 10 to prepare the respective ketone under column IX.

IX 6,10,10-trimethylundec-3-en-2-one
6,10,10-trimethyldodec-3-en-2-one
6,9,9-trimethyldec-3-en-2-one
6,11,11-trimethyldodec-3-en-2-one
7,11,11-trimethyldodec-3-en-2-one

EXAMPLE 20

A. To magnesium propynlide (15 g.) in 150 ml. of ether is slowly added 0.3 moles of 3,7-dimethyl-1-octanal at 0° and the mixture then stirred overnight. Saturated aqueous ammonium chloride is added and the layers separated. The organic phase, combined with ether backwashings of aqueous phase, is washed with water, dried and solvent evaporated to yield 6,10-dimethylundec-2-yn-4-ol which can be purified by distillation or chromatography.

B. A mixture of 18.5 g. of 6,10-dimethylundec-2-yn-4-ol, 80 g. of triethylorthacetate and 0.75 g. of propionic acid is refluxed under a spinning band column to remove ethanol as it is formed. After the elimination of ethanol is about complete, the crude reaction product is distilled under vacuum to yield ethyl 3,7,11-trimethyldodeca-3,4-dienoate. Alternatively, the crude reaction product is purified by chromatography on silica.

C. A solution of 1.0 g. of the allenic ester of part B in 20 ml. of ethanol is treated with 4 ml. of aqueous 2N sodium hydroxide and left at room temperature for several minutes. The mixture is then poured into pentane and washed with saturated brine and separated. Evaporation of the organic phase yield ethyl 3,7,11-trimethyldodeca-2,4-dienoate.

EXAMPLE 21

The process of part A of Example 20 is repeated using each of the aldehydes under column XI to produce the respective alkynyl alcohol under column XII.

XI 3,7-dimethylnonan-1-al
3,7,7-trimethyloctan-1-al
3,7,7-trimethylnonan-1-al
2,5-dimethylhexan-1-al
3,6-dimethylheptan-1-al

XII 6,10-dimethyldodec-2-yn-4-ol
6,10,10-trimethylundec-2-yn-4-ol
6,10,10-trimethyldodec-2-yn-4-ol
5,8-dimethylnon-2-yn-4-ol
6,9-dimethyldec-2-yn-4-ol The alkynyl alcohols under column XII are reacted with triethylorthoacetate to produce the respective allenic ester under column XIII which are rearranged to produce the esters under column XIV.

XIII ethyl 3,7,11-trimethyltrideca-3,4-dienoate
ethyl 3,7,11,11-tetramethyldodeca-3,4-dienoate
ethyl 3,7,11,11-tetramethyltrideca-3,4-dienoate
ethyl 3,6,9-trimethyldeca-3,4-dienoate
ethyl 3,7,10-trimethylundeca-3,4-dienoate

XIV ethyl 3,7,11-trimethyltrideca-2,4-dienoate
ethyl 3,7,11,11-tetramethyldodeca-2,4-dienoate
ethyl 3,7,11,11-tetramethyltrideca-2,4-dienoate
ethyl 3,6,9-trimethyldeca-2,4-dienoate
ethyl 3,7,10-trimethylundeca-2,4-dienoate

EXAMPLE 22

Each of the alkynyl alcohols of Examples 20 and 21 is reacted with trimethylorthoacetate to produce the respective allenic ester under column XVI, which is rearranged to produce the respective 2,4-dienoate under column XVII.

XVI methyl 3,7,11-trimethyldodeca-3,4-dienoate
methyl 3,7,11-trimethyltrideca-3,4-dienoate
methyl 3,7,11,11-tetramethyldodeca-3,4-dienoate
methyl 3,7,11,11-tetramethyltrideca-3,4-dienoate
methyl 3,6,9-trimethyldeca-3,4-dienoate
methyl 3,7,10-trimethylundeca-3,4-dienoate

XVII methyl 3,7,11-trimethyldodeca-2,4-dienoate
methyl 3,7,11-trimethyltrideca-2,4-dienoate
methyl 3,7,11,11-tetramethyldodeca-2,4-dienoate
methyl 3,7,11,11-tetramethyltrideca-2,4-dienoate
methyl 3,6,9-trimethyldeca-2,4-dienoate
methyl 3,7,10-trimethylundeca-2,4-dienoate

EXAMPLE 23

Sodium ethoxide (9 g. sodium in 600 ml. of ethanol) is added slowly to a mixture of 42 g. of dihydrocitronellal and 75 g. of diethyl 3-ethoxycarbonyl-2-methylprop-2-enyl phosphonate (about 49% trans) in one liter of dimethylformamide, under nitrogen and at 0°, with stirring. The mixture is allowed to stand overnight at about 5° and the reaction worked up by extraction with ether, washing with water and brine and filtering through Florisil to yield ethyl 3,7,11-trimethyldodeca-2,4-dienoate as a cis/trans mixture, mostly trans,trans.

EXAMPLE 24

Sodium methoxide (1.2 g. of sodium and 30 ml. of methanol) is added slowly to a mixture of 5 g. of dihydrocitronellal and 10 g. of diethyl 3-methoxycarbonyl-2-methylprop-2-enyl phosphonate (about 77% trans) in 50 ml. of dimethylformamide, under nitrogen and at about 0°, with stirring. After addition is complete, the reaction is left three hours at room temperature and then worked up by extraction with hexane/ether to yield cis/trans methyl 3,7,11-trimethyldodeca-2,4-dienoate, mostly the trans,trans iosmer.

EXAMPLE 25

To a mixture of 1.5 g. of dihydrocitronellal, 2.7 g. of diethyl 3-ethoxycarbonyl-2-methylprop-2-enyl phosphonate and 5 ml. of dimethylformamide, under nitrogen and at 0°, with stirring, is added slowly sodium methoxide (250 mg. sodium and 5 ml. of methanol). After addition is complete, the reaction is left two hours at room temperature and then worked up by extraction with ether/hexane to yield methyl 3,7,11-trimethyldodeca-2,4-dienoate.

EXAMPLE 26

To a mixture of 30 g. of dihydrocitronellal, 44 g. of diethyl 3-ethoxycarbonyl-2-ethylprop-2-enyl phosphonate and 200 ml. of dimethylformamide, under nitrogen at 0° and with stirring, is added slowly sodium ethoxide (4.6 g. sodium in 100 ml. of ethanol). After addition is complete, the reaction is left at room temperature for two hours and then worked up by extraction with hexane to yield ethyl 3-ethyl-7,11-dimethyldodeca-2,4-dienoate.

EXAMPLE 27

To 0.6 g. of recrystallized trans,trans 3,7,11-trimethyldodeca-2,4-dienoic acid in 10 ml. of dry benzene is added 0.23 ml. of oxalyl chloride at room temperature with stirring. After two hours, isopropanol (2 ml.) is added and the mixture allowed to stand at room temperature for about two hours. Ether and saturated sodium bircarbonate is added and the organic phase separated. The organic phase is washed with aqueous sodium bicarbonate, saturated sodium chloride, dried over calcium sulfate and evaporated to yield trans,trans isopropyl 3,7,11-trimethyldodeca-2,4-dienoate containing a small amount of cis,trans isomer.

EXAMPLE 28

To 0.6 g. of trans,trans 3,7,11-trimethyldodeca-2,4-dienoic acid in 10 ml. of dry benzene is added 0.23 ml. of oxalyl chloride at room temperature. After about two hours, there is added 0.25 ml. of 3-thiabutan-1-ol and the reaction allowed to stand for about two hours. The reaction is worked up as in Example 27 to yield trans,trans 3'-thiabutanyl 3,7,11-trimethyldodeca-2,4-dienoate (containing a small amount of cis,trans).

The above process is repeated using two ml. of $CF_3CH_2OH$ in place of 3-thiabutan-1-ol to yield trifluoroethyl 3,7,11-trimethyldodeca-2,4-dienoate.

EXAMPLE 29

To 350 ml. of ethanol, 105 ml. of water and 70 ml. of 50% aqueous sodium hydroxide is added 46.5 g. of ethyl 3,7,11-trimethyldodeca-2,4-dienoate (40% cis, trans and 60% trans,trans). The mixture is refluxed for about 19 hours. After cooling, ethanol is removed under reduced pressure and water added followed by extraction with ether to yield 3,7,11-trimethyldodeca-2,4-dienoic acid containing about 58% trans,trans isomer. Conversion of the thus-obtained acid to the benzylisothiouronium salt recrystallized from aqueous methanol, and regeneration of the acid with ether-aqueous hydrochloric acid provides crystalline trans,-trans 3,7,11-trimethyldodeca-2,4-dienoic acid.

EXAMPLE 30

To a solution of 0.5 g. of trans/cis 3,7,11-trimethyldodeca-2,4-dienoic acid in 15 ml. of benzene is added with stirring an equivalent amount of potassium bicarbonate. The mixture is stirred until the evolution of carbon dioxide ceases and then evaporated to yield potassium 3,7,11-trimethyldodeca-2,4-dienoate.

Alternatively, acid salts can be prepared by titrating the acid with an organic solution or an aqueous organic solution containing the metal desired.

By use of the foregoing procedure, the metal salts of each of the acids of formula B can be prepared.

EXAMPLE 31

By use of the procedures hereinabove, see Example 23 and 24, for example, each of the aldehydes under column XVIII is reacted with the carbanion of diethyl 3-ethoxycarbonyl-2-methylprop-2-enyl phosphonate to prepare the respective ethyl ester under column XIX.

XVIII 3,7-dimethyldecan-1-al
3,7-dimethylundecan-1-al
3,5,6-trimethylheptan-1-al
3,8-dimethylnonan-1-al 2,6-dimethylheptan-1-al
4,7,8-trimethylnonan-1-al
4,8-dimethyldecan-1-al
2,9-dimethyldecan-1-al
2,5,6-trimethylheptan-1-al
2,6,6-trimethylheptan-1-al
2,5,5-trimethylhexan-1-al

XIX ethyl 3,7,11-trimethyltetradeca-2,4-dienoate
ethyl 3,7,11-trimethylpentadeca-2,4-dienoate
ethyl 3,7,9,10-tetramethylundeca-2,4-dienoate
ethyl 3,7,12-trimethyltrideca-2,4-dienoate
ethyl 3,6,10-trimethylundeca-2,4-dienoate
ethyl 3,8,11,12-tetramethyltrideca-2,4-dienoate
ethyl 3,8,11-trimethyltetradeca-2,4-dienoate
ethyl 3,6,13-trimethyltetradeca-2,4-dienoate
ethyl 3,6,9,10-tetramethylundeca-2,4-dienoate
ethyl 3,6,10,10-tetramethylundeca-2,4-dienoate
ethyl 3,6,9,9-tetramethyldeca-2,4-dienoate

EXAMPLE 32

A. Eightly ml. of a 3M solution of methylmagnesium bromide in ether is added slowly to 31 g. of dihydrocitronellal in 250 ml. of dry ether. The mixture is heated at reflux for about 1 hour, cooled to 0° and treated with saturated aqueous ammonium chloride until reaction subsides. The organic layer is separated and the aqueous layer extracted with ether. The organic layer and ether extracts are combined, washed with water and brine and dried over magnesium sulfate. Evaporation of the solvent gives 4,8-dimethylnonan-2-ol.

B. A solution of 47 g. of 4,8-dimethylnonan-2-ol in 250 ml. of methylene chloride is cooled to about 10° as a solution of 46.4 g. of sodium dichromate in 125 ml. of water is added. The mixture is maintained at about 10° as a solution of 46.3 g. of sulfuric acid in 100 ml. of water is added over about 45 minutes. The mixture is allowed to attain room temperature and, after about 3 hours, the organic layer is separated and the aqueous layer is extracted with methylene chloride. The combined organic materials are washed with saturated potassium bicarbonate, water and saturated sodium chloride, dried over magnesium sulfate and evaporated to yield 4.8-dimethylnonan-2-one.

The Grignard reaction of part A is repeated using each of 3,7-dimethylnonan-1-al, 3-methyl-7-ethylnonan-1-al, 3,7,7-trimethyloctan-1-al, 3,7,7-trimethylnonan-1-al, 3,6,7-trimethyloctan-1-al, 3,7,8-trimethylnonan-1-al, 2,4,5-trimethylhexan-1-al, 2,5-dimethylhexan-1-al, 3,5,6-trimethylheptan-1-al, 3,6-dimethylheptan-1-al, 2,6-dimethylheptan-1-al and 2,5,6-trimethylheptan-1-al in place of dihydrocitronellal to yield the respective secondary alcohol 4,8-dimethyldecan-2-ol
4-methyl-8-ethyldecan-2-ol
4,8,8-trimethylnonan-2-ol
4,8,8-trimethyldecan-2-ol
4,7,8-trimethylnonan-2-ol
4,8,9-trimethyldecan-2-ol
3,5,6-trimethylheptan-2-ol
3,6-dimethylheptan-2-ol
4,6,7-trimethyloctan-2-ol
4,7-dimethyloctan-2-ol
3,7-dimethyloctan-2-ol
3,6,7-trimethyloctan-2-ol Each of the above alcohols is oxidized to prepare the respective ketone 4,8-dimethyldecan-2-one
4-methyl-8-ethyldecan-2-one
4,8,8-trimethylnonan-2-one
4,8,8-trimethyldecan-2-one
4,7,8-trimethylnonan-2-one
4,8,9-trimethyldecan-2-one
3,5,6-trimethylheptan-2-one
3,6-dimethylheptan-2-one
4,6,7-trimethyloctan-2-one
4,7-dimethyloctan-2-one
3,7-dimethyloctan-2-one
3,6,7-trimethyloctan-2-one C. Each of the ketones of part B is reacted with the carbanion of diethyl 3-ethoxycarbonyl-2-methylprop-2-enyl phosphonate according to procedures above to prepare the respective 2,4-dienoate i.e.

ethyl 3,5,7,11-tetramethyldodeca-2,4-dienoate
ethyl 3,5,7,11-tetramethyltrideca-2,4-dienoate
ethyl 3,5,7-trimethyl-11-ethyltrideca-2,4-dienoate
ethyl 3,5,7,11,11-pentamethyldodeca-2,4-dienoate
ethyl 3,5,7,11,11-pentamethyltrideca-2,4-dienoate
ethyl 3,5,7,10,11-pentamethyldodeca-2,4-dienoate
ethyl 3,5,7,11,12-pentamethyltrideca-2,4-dienoate
ethyl 3,5,6,8,9-pentamethyldeca-2,4-dienoate
ethyl 3,5,6,9-tetramethyldeca-2,4-dienoate
ethyl 3,5,7,9,10-pentamethylundeca-2,4-dienoate
ethyl 3,5,7,10-tetramethylundeca-2,4-dienoate
ethyl 3,5,6,10-tetramethylundeca-2,4-dienoate
ethyl 3,5,6,9,10-pentamethylundeca-2,4-dienoate

EXAMPLE 33

A. Each of the ketones of part B of Example 32 is reacted with the carbanion of diethyl 3-ethoxycarbonyl-1,2-dimethylprop-2-enylphosphonate to prepare the respective 2,4-dienoate -i.e.

ethyl 3,4,5,7,11-pentamethyldodeca-2,4-dienoate
ethyl 3,4,5,7,11-pentamethyltrideca-2,4-dienoate
ethyl 3,4,5,7-tetramethyl-11-ethyltrideca-2,4-dienoate
ethyl 3,4,5,7,11,11-hexamethyldodeca-2,4-dienoate
ethyl 3,4,5,7,11,11-hexamethyltrideca-2,4-dienoate
ethyl 3,4,5,7,10,11-hexamethyldodeca-2,4-dienoate
ethyl 3,4,5,7,11,12-hexamethyltrideca-2,4-dienoate
ethyl 3,4,5,6,8,9-hexamethyldeca-2,4-dienoate
ethyl 3,4,5,6,9-pentamethyldeca-2,4-dienoate
ethyl 3,4,5,7,9,10-hexamethylundeca-2,4-dienoate
ethyl 3,4,5,7,10-pentamethylundeca-2,4-dienoate
ethyl 3,4,5,6,10-pentamethylundeca-2,4-dienoate
ethyl 3,4,5,6,9,10-hexamethylundeca-2,4-dienoate B. Each of the aldehydes under col. I is reacted with the carbanion of diethyl 3-ethoxycarbonyl-1,2-dimethylprop-2-enyl phosphonate to prepare the respective 2,4-dienoate, i.e.

ethyl 3,4,7,11-tetramethyldodeca-2,4-dienoate
ethyl 3,4,7,11-tetramethyltrideca-2,4-dienoate
ethyl 3,4,11-trimethyl-7-ethyltrideca-2,4-dienoate
ethyl 3,4,7,10-tetramethylundeca-2,4-dienoate
ethyl 3,4,6,9-tetramethyldeca-2,4-dienoate
ethyl 3,4,6,9-tetramethylundeca-2,4-dienoate
ethyl 3,4,8,12-tetramethyltrideca-2,4-dienoate
ethyl 3,4,8,13-tetramethyltetradeca-2,4-dienoate ethyl 3,4,7,13-tetramethyltetradeca-2,4-dienoate By use of the procedure of part B of this example, other aldehydes of formula I ($R^{13}$ is hydrogen are converted into the respective ester of formula B' wherein $R^{13}$ is hydrogen and $R^{12}$ is methyl or other lower alkyl. Similarly following the procedure of part A of this example, other ketones of formula I ($R^{13}$ is lower alkyl) are converted into esters of formula B' wherein each of $R^{12}$ and $R^{13}$ is lower alkyl. Using the process of part C of Example 32, other esters of the present invention of formula B' wherein $R^{12}$ is hydrogen and $R^{13}$ is methyl or other lower alkyl can be prepared using a ketone of formula I ($R^{13}$ is lower alkyl) as the precursor.

C. Each of the esters of this example and Example 32 can be hydrolyzed to the free acid according to the procedure of Example 5 or 29. The acid or acid chloride can be reacted with an alcohol such as isopropanol, t-butanol, benzyl alcohol, and the like to prepare other esters of the present invention.

EXAMPLE 34

Following the process of Example 27, there is prepared the following acid chlorides by the reaction of oxalyl chloride with the free acid.

3,7,11-trimethyltrideca-2,4-dienoyl chloride
3,11-dimethyl-7-ethyltrideca-2,4-dienoyl chloride
3,7-dimethyl-11-ethyltrideca-2,4-dienoyl chloride
3,7,11,11-tetramethyldodeca-2,4-dienoyl chloride
3,7,11,11-tetramethyltrideca-2,4-dienoyl chloride
3,7,10,11-tetramethyldodeca-2,4,-dienoyl chloride
3,7,10,11-tetramethyltrideca-2,4-dienoyl chloride
3,7,11,12-tetramethyltrideca-2,4-dienoyl chloride
3,7,11-trimethyltetradeca-2,4-dienoyl chloride
3,6,8,9-tetramethyldeca-2,4-dienoyl chloride
3,6,9-trimethyldeca-2,4-dienoyl chloride
3,6,9,9-tetramethyldeca-2,4-dienoyl chloride
3,7,9,10-tetramethylundeca-2,4-dienoyl chloride
3,7,10-trimethylundeca-2,4-dienoyl chloride
3,7,10,10-tetramethylundeca-2,4-dienoyl chloride
3,6,10-trimethylundeca-2,4-dienoyl chloride
3,6,9,10-tetramethylundeca-2,4-dienoyl chloride
3,6,10,10-tetramethylundeca-2,4-dienoyl chloride
3,7,12-trimethyltrideca-2,4-dienoyl chloride
3,8,11-trimethyltrideca-2,4-dienoyl chloride Each of the above acid chlorides is reacted with isopropanol according to the procedure of Example 27 to prepare the respective isopropyl ester.

isopropyl 3,7,11-trimethyltrideca-2,4-dienoate
isopropyl 3,11-dimethyl-7-ethyltrideca-2,4-dienoate
isopropyl 3,7-dimethyl-11-ethyltrideca-2,4-dienoate
isopropyl 3,7,11,11-tetramethyldodeca-2,4-dienoate
isopropyl 3,7,11,11-tetramethyltrideca-2,4-dienoate
isopropyl 3,7,10,11-tetramethyldodeca-2,4-dienoate
isopropyl 3,7,10,11-tetramethyltrideca-2,4-dienoate
isopropyl 3,7,11,12-tetramethyltrideca-2,4-dienoate
isopropyl 3,7,11-trimethyltetradeca-2,4-dienoate
isopropyl 3,6,8,9-tetramethyldeca-2,4-dienoate
isopropyl 3,6,9-trimethyldeca-2,4-dienoate
isopropyl 3,6,9,9-tetramethyldeca-2,4-dienoate
isopropyl 3,7,9,10-tetramethylundeca-2,4-dienoate
isopropyl 3,7,10-trimethylundeca-2,4-dienoate
isopropyl 3,7,10,10-tetramethylundeca-2,4-dienoate
isopropyl 3,6,10-trimethylundeca-2,4-dienoate
isopropyl 3,6,9,10-tetramethylundeca-2,4-dienoate
isopropyl 3,6,10,10-tetramethylundeca-2,4-dienoate
isopropyl 3,8,11-trimethyltrideca-2,4-dienoate By the reaction of the acid chlorides listed above in this example with other alcohols in place of isopropanol, the respective ester is obtained. For example, the use of each of methanol, t-butyl alcohol, n-propanol, s-butyl alcohol, isobutyl alcohol, 3,3-dimethylpentan-1-ol, 2-methylpentan-1-ol, hexan-2-ol, 3-methylpentan-1-ol, cyclopentanol, p-ethylphenol, β-phenylethanol, p-methylbenzyl alcohol, 2-fluoroethanol, 2,2-dichloroethanol, 2,2,2-trichloroethanol and 2-chloropropan-1-ol in place of isopropanol gives methyl 3,7,11-trimethyltrideca-2,4-dienoate
t-butyl 3,7,11-trimethyltrideca-2,4-dienoate
n-propyl 3,7,11-trimethyltrideca-2,4-dienoate
s-butyl 3,7,11-trimethyltrideca-2,4-dienoate
isobutyl 3,7,11-trimethyltrideca-2,4-dienoate
neopentyl 3,7,11-trimethyltrideca-2,4-dienoate
2'-methylpent-1'-yl 3,7,11-trimethyltrideca-2,4-dienoate
hex-2'-yl 3,7,11-trimethyltrideca-2,4-dienoate
3'-methylpent-1'-yl 3,7,11-trimethyltrideca-2,4-dienoate
cyclopentyl 3,7,11-trimethyltrideca-2,4-dienoate
p-ethylphenyl 3,7,11-trimethyltrideca-2,4-dienoate
β-phenylethyl 3,7,11-trimethyltrideca-2,4-dienoate
p-methylbenzyl 3,7,11-trimethyltrideca-2,4-dienoate
2'-fluoroethyl 3,7,11-trimethyltrideca-2,4-dienoate
2',2'-dichloroethyl 3,7,11-trimethyltrideca-2,4-dienoate
2',2',2'-trichloroethyl 3,7,11-trimethyltrideca-2,4-dienoate
2'-chloroprop-1'-yl 3,7,11-trimethyltrideca-2,4-dienoate In the same way, the corresponding 3,7,11-trimethyldodeca-2,4-dienoic acid esters can be prepared from 3,7,11-trimethyldodeca-2,4-dienoyl chloride as well as other esters of the present invention of formula A.

EXAMPLE 35

Using the procedures of Example 27, each of hexa-2,4-dien-1-ol, prop-2-en-1-ol, but-2-en-1-ol, but-2-yn-1-ol, prop-2-yn-1-ol and 4-methylpent-2-yn-1-ol is reacted with the acid chloride of trans, trans 3,7,11-trimethyldodeca-2,4-dienoic acid to prepare the respective trans, trans ester, that is hexa-2',4'-dienyl 3,7,11-trimethyldodeca-2,4-dienoate,
prop-2'-enyl 3,7,11-trimethyldodeca-2,4-dienoate,
but-2'-enyl 3,7,11-trimethyldodeca-2,4-dienoate
but-2'-yn-1'-yl 3,7,11-trimethyldodeca-2,4-dienoate,
prop-2'-yn-1'-yl 3,7,11-trimethyldodeca-2,4-dienoate, and
4'-methylpent-2'-yn-1'-yl 3,7,11-trimethyldodeca-2,4-dienoate.

EXAMPLE 36

Following the procedure of Example 27, each of (+) sec.-butyl alcohol and (−) sec.-butyl alcohol is reacted with the acid chloride of trans, trans 3,7,11-trimethyldodeca-2,4-dienoic acid to prepare (+) sec.-butyl 3,7,11-trimethyldodeca-2(trans), 4(trans)dienoate and (−) sec. butyl 3,7,11-trimethyldodeca-2(trans), 4(trans)dienoate.

Each of penta-2',3'-dienyl 3,7,11-trimethyldodeca-2,4-dianoate, pent-2'-yn-1'-yl 3,7,11-trimethyldodeca-2,4-dienoate and but-3'-en-1'-yl 3,7,11-trimethyldodeca-2,4-dienoate is prepared using penta-2,3-dien-1-ol, pent-2-yn-1-ol and but-3-en-1-ol in the process of Example 27 in place of isopropanol.

EXAMPLE 37

3,7,11-trimethyltrideca-2,4-dienoyl chloride (18 g.) is added slowly to ethyl lead mercaptide (13.4 g) covered with ether at 0°. The mixture is allowed to stand overnight and then is filtered. The filtrate is evaporated under reduced pressure to yield ethyl 3,7,11-trimethyl-thioltrideca-2,4-dienoate which can be purified by chromatography.

EXAMPLE 38

To a solution of 25.4 g. of 3,7,11-trimethyltrideca-2,4-dienoyl chloride in ether at −20° is added 12.4 g. of ethylmercaptan and 11.8 g. of pyridine. The mixture is allowed to stand at zero degrees for about 36 hours and then is diluted with ether and water and separated. The ether phase is washed with dilute aqueous sodium hydroxide, dilute hydrochloric acid and then water, dried and solvent removed to yield ethyl 3,7,11-trimethyl-thioltrideca-2,4-dienoate.

The process of this example is repeated using each of the acid chlorides of Example 17 to prepare the respective thiol ester, i.e. - ethyl 3,7,11-trimethyl-thioldodeca-2,4-dienoate
ethyl 3,11-dimethyl-7-ethyl-thioltrideca-2,4-dienoate
ethyl 3,7,10-trimethyl-thiolundeca-2,4-dienoate
ethyl 3,6,9-trimethyl-thioldeca-2,4-dienoate
ethyl 3,6,9-trimethyl-thiolundeca-2,4-dienoate
ethyl 3,8,12-trimethyl-thioltrideca-2,4-dienoate
ethyl 3,8,13-trimethyl-thioltetradeca-2,4-dienoate Similarly, each of 3,7,11,11-tetramethyldodeca-2,4-dienoyl chloride, 3,7,11,11-tetramethyltrideca-2,4-dienoyl chloride, 3,7,10,11-tetramethyldodeca-2,4-dienoyl chloride, 3,7,9,10-tetramethyldodeca-2,4-dienoyl chloride, and 3,6,8,9-tetramethyldodeca-2,4-dienoyl chloride is converted into the corresponding thiol ester, i.e. - ethyl 3,7,11,11-tetramethyl-thioldodeca-2,4-dienoate
ethyl 3,7,11,11-tetramethyl-thioltrideca-2,4-dienoate
ethyl 3,7,10,11-tetramethyl-thioldodeca-2,4-dienoate
ethyl 3,7,9,10-tetramethyl-thiolundeca-2,4-dienoate
ethyl 3,6,8,9-tetramethyl-thiolundeca-2,4-dienoate Methylmercaptan is reacted with each of the dienoyl-chlorides above using the procedure of this example except that the reaction mixture is prepared at about −10° and the reaction is carried out in a sealed vessel to prepare the respective methyl thiol esters, e.g. methyl 3,7,11-trimethyl-thioltrideca-2,4-dienoate, methyl 3,7,11-trimethyl-thioldodeca-2,4-dienoate, methyl 3,11-dimethyl-7-ethyl-thioltrideca-2,4-dienoate, etc.

EXAMPLE 39

To 0.55 g. of 3,7,11-trimethyldodeca-2,4-dienoic acid in 10 ml. of dry benzene is added 0.21 ml. of oxalyl chloride. The mixture is stirred occasionally at room temperature for about 2.5 hours. The mixture is cooled in cold water and then 0.18 ml. of ethylmercaptan is added with stirring. The mixture is then stirred at room temperature for about 24 hours. Ether and saturated sodium bicarbonate is added and the organic phase separated. The organic phase is washed with aqueous sodium bicarbonate, saturated sodium chloride, dried over calcium sulfate and evaporated to yield ethyl 3,7,11-trimethyl-thioldodeca-2,4-dienoate.

Thiol esters of formula A are prepared using each of n-propyl mercaptan, isopropyl mercaptan, isobutyl mercaptan, s-butyl mercaptan, n-butyl mercaptan, benzyl mercaptan, cyclopentyl mercaptan, β-phenylethyl mercaptan, t-amyl mercaptan and n-hexyl mercaptan in reaction with 3,7,11-trimethyldodeca-2,4-dienoyl chloride or the sodium salt of 3,7,11-trimethyldodeca-2,4-dienoic acid to yield n-propyl 3,7,11-trimethyl-thioldedeca-2,4-dienoate
isopropyl 3,7,11-trimethyl-thioldodeca-2,4-dienoate
isobutyl 3,7,11-trimethyl-thioldodeca-2,4-dienoate
s-butyl 3,7,11-trimethyl-thioldodeca-2,4-dienoate
n-butyl 3,7,11-trimethyl-thioldodeca-2,4-dienoate
benzyl 3,7,11-trimethyl-thioldodeca-2,4-dienoate
cyclopentyl 3,7,11-trimethyl-thioldodeca-2,4-dienoate
β-phenylethyl 3,7,11-thioldodeca-2,4-dienoate
t-amyl 3,7,11-thioldodeca-2,4-dienoate
n-hexyl 3,7,11-thioldodeca-2,4-dienoate Thiol acids of formula A are prepared by the reaction of hydrogen sulfide with an acid chloride of formula A. For example, a solution of 3,7,11-trimethyldodeca-2,4-dienoyl chloride in benzene is added to benzene saturated with hydrogen sulfide and the mixture allowed to stand for about 2 hours with continuous introduction of nitrogen. The reaction is worked up as described above to yield 3,7,11-trimethyl-thioldodeca-2,4-dienoic acid.

EXAMPLE 40

One gram of 5% palladium-on-carbon and 8 g. of 2,5-dimethylhex-4-en-1-al is stirred in 50 ml. of ethanol under excess hydrogen at one atomsphere pressure and at room temperature until the theoretical amount of hydrogen is absorbed (about 24 hours). Then, 2 ml. of dichloromethane is added and the mixture filtered. The filtrate is concentrated under reduced pressure to yield 2,5-dimethylhexan-1-al.

Similarly, each of 2,5-dimethylhept-4-en-1-al, 2-methyl-5-ethylhept-4-en-1-al, 6-methylhept-5-en-2-one, 6-methyloct-5-en-2-one and 6-ethyloct-5-en-2-one is hydrogenated to prepare the respective saturated compound.

To a suspension of 21 grams of methoxymethyltriphenylphosphonium chloride in 200 ml. of absolute ether is added under nitrogen at room temperature a solution of 60 mmoles of phenyllithium in ether. After about 10 minutes, the mixture is cooled to −30° and 6 grams of 2,5-dimethylhexan-1-al in ether is added slowly. After about 12 hours at room temperature, the mixture is filtered and the filtrate evaporated. The concentrate is dissolved in aqueous tetrahydrofuran containing a small amount of dilute hydrochloric acid and stirred at room temperature for about 48 hours. The mixture is worked up in ether to yield 3,6-dimethylheptan-1-al which is purified by chromatography.

By repeating the foregoing Wittig reaction followed by hydrolysis using each of 3,6-dimethylheptan-1-al, 6-methyloct-5-en-2-one and 7-ethylnonan-3-one as the starting material, there is prepared 4,7-dimethyloctan-1-al, 2,6-dimethyloctan-1-al, and 2,6-diethyloctan-1-al.

By the use of the above process, the compounds of formula X can be converted into aldehydes of formula I'.

Suitable procedure for oxidation of alcohols to prepare aldehydes is as follows:

Five grams of 3,7,7-trimethyloctan-1-ol in 50 ml. of dry pyridine is added to a mixture of chromic acid (5 g.) in pyridine (50 ml.) with stirring. After two hours, isopropanol (10 ml.) is added and after a further 30 minutes, the mixture is diluted with 0.5% aqueous potassium hydroxide solution and extracted with ether. The ethereal extract is washed, dried and evaporated to yield 3,7,7-trimethyloctan-1-al.

Another synthesis for acids and esters of formula B is the reaction of a ketone of formula III hereinabove with ketene to form the acid (B' $R^7$ is hydrogen) which can be subjected to esterification prior to isolation of the acid, if desired, with an alcohol such as methanol, ethanol or isopropanol according to the ester moiety desired. In the practice of this synthesis, gaseous ketene is passed through an excess of the ketone (III) containing a catalytic amount of an acid catalyst. The ketene and ketone can be diluted with an organic solvent inert to the reaction if desired. Suitable conditions and catalysts for the practice of this synthesis is described by Boese, Jr., U.S. Pat. No. 2,382,464.

Three groups of 30 each of Aedes aegypti, fourth instar larvae, in 50 ml. of tapwater containing a few drops of liver powder suspension, room temperature of 28° and photoperiod of 18 hours, are treated with ethyl 3,7,11-trimethyldodeca-2,4-dienoate (about 98% trans, trans,) using 50 microliters of acetone as the carrier at three different dosage levels. A fourth group is maintained under identical conditions. Each group is scored after 7 days by the following system: 0 = normal adult, completely emerged (free or floating); 1 = abnormal adult, nonviable; 2 = incompletely emerged adult; 3 = dead pupa; and 4 = dead larvae. For each group the total number of animals in classes 1–4 is divided by 30 to determine the percentage result. The $ID_{50}$ is computed by plotting on semi-logarithmic paper, the dose on the horizontal axis and the percentage response on the verticle axis. The $ID_{50}$ was determined to be less than 1.0 ppm. Each of the larvae of the control group developed into normal adults. The compounds, methyl 3,7,11-trimethyldodeca-2,4-dienoate (about 93% trans, trans), ethyl 3,7,11-trimethyl-thiol-dodeca-2,4-dienoate (mostly trans, trans), and ethyl 3,7,11-trimethyldodeca-2,4-dienoate (about 91% cis, trans) were tested in the same way and found to have an $ID_{50}$ of less than 1.0 ppm.

Three groups of 20 each of Tenebrio molitor pupae (less than 24 hours old) maintained on wheat germ and bran, 25° room, 18 hours light, are treated at 0.1, 1.0 and 10.0 μg with isopropyl 3,7,11-trimethyldodeca-2,4-dienoate (predominantly all trans) using acetone carrier. The active agent is placed on the 5th abdominal sterinite using a syringe. The $ID_{50}$ was less than 0.1 μg.

Concentrate suitable for filed application, with or without dilution depending upon spraying apparatus, can be formulated as follows (percentage by weight).

| | |
|---|---|
| Ethyl 3,7,11-trimethyldodeca-2,4-dienoate (80% trans) | 50% |
| Emcol N-140B | 12% |
| Emcol T-180 | 2% |
| Xylene | 36% |

-continued

| | |
|---|---|
| Ethyl 3,7,11-trimethyldodeca-2,4-dienoate (80% trans) | 50% |
| Emcol N-140B | 8% |
| Emcol T-180 | 1.3% |
| Xylene | 40.7% |

Emcol N-140B, a blend of polyoxyethylene ethers and oil-soluable sulfonates, and Emcol T-180 are tradenames for surfactants of Witco Chemical, New York, N.Y.

The above concentrates can be applied without dilution using ultra-low volume sprayers or can be diluted with, for example, water before application. Dilutions containing the active component within the range of about 0.0001% to 10% are generally employed. A dilution of ether of the above concentrates with water to provide 1.0% of the active component, when applied to locals infested with immature peach aphids provides effective control.

A fine dust is prepared of 10 parts of isopropyl 3,7,11-trimethyldodeca-2,4-dienoate and 90 parts synthetic fine silica, by weight, by blending in a Waring Blendor. The fine dust is particularly useful for application to broadleaf plants for the control of cabbage looper, turnip aphids, and squash vine borer.

Ethyl 3,7,11-trimethyldodeca-2,4-dienoate (64% trans, trans) is put neat on wheat to provide a concentration of 5 ppm and superblended. The treated wheat is placed in a large glass container and 20 viable adult Lesser grain borers (Rhyzopertha dominica) introduced. The same quantity of untreated wheat is placed in a large glass container and 20 viable adult Lesser grain borers introduced. The two groups are maintained under identical conditions for 8 weeks. In the case of the treated grain, the 20 adults survived and the grain contained a few larvae and non-viable pupa, the larvae were not active and instead existed in diapause or pre-pupal like state - indicates essentially complete control for protection of the grain. The untreated grain (control) — all adults survived and the grain was infested with hundreds of active larvae. The same treatment was made of other stored grain pests — i.e. Rice weevil, Indian meal moth and almond moth and provided essentially complete control by inhibiting adult emergence with larvae being inactive and existing in diapause or pre-pupal like state.

In some applications of the compounds of the present invention, it is advantageous to formulate the active compound such as an ester of formula B with a polymeric material or a combination of polymer, filler, plasticizer and stabilizers. Thus, in the use of, e.g., and ester of formula B as a Control agent for mosquitos, the active compound can be blended with a polymer such as polyvinyl chloride and copolymers of polyvinyl chloride or ethylenepropylenediene terpolymers as described in U.S. Pat. No. 3,590,119 to extend the life and effectiveness for control of mosquito larvae. The density of the blended or encapsulated material can be gauged so as to make it available at the most optimum position. Polymeric blends and encapsulation of the active compounds of the present invention can be usefully applied to provide effective control of insects which harbor in the surface or under the surface of the soil as immature insects. Suitable polymers, blending techniques and encapsulation methods are described in U.S. Pat. No. 2,777,824; 3,055,397; 3,318,769;

3,393,990; 3,499,962; 3,551,556; 3,565,818; 3,565,599; 3,565,819; and 3,577,515.

Although not intending to be limited by a theoretical explanation, the effectiveness of the compounds of the present invention to control insects is attributed to the property of these novel compounds to mimic the activity of juvenile hormone as demonstrated herein. While the methods of applying and carriers for conventional insecticides are usually adaptable to the practical use of the compounds of the present invention, the mechanism of action of these novel compounds is unlike that of conventional insects. Whereas conventional insecticides are dependent upon direct knockdown effect, toxity effect or paralyzing effect; the compounds of this invention achieve control by reason of their ability to inhibit metamorphosis, inhibit reproduction due to abnormal development, break diapause at an unfavorable time, or act as a direct insecticide particularly at the embryo stage and larvae stage. Treatment of insects in accordance with the present invention can be achieved via ingestion of the active compound in the normal food of the insect and by topical application that is by contact of the epidermis of the insect as by spraying the insect and habitat of the insect or exposure to vapors of the active compound which penetrate into the insect.

The compound of the present invention can be used in conjunction with other juvenile hormone active substances and conventional insecticides to obtain a broader spectrum of activity or to provide more immediate effect on very heterogeneous populations. Typical insecticides which may be combined with the compounds of the present invention are Malathion, Sevin, Vapona, synthetic and natural pyrethrins, and the like and usually within the ratio of between 10:1 to 1:10, by weight.

The following is an example of a granule formation in accordance with the present invention:

| Attaclay 15–30 | 80% |
|---|---|
| Propylene glycol | 1% |
| Compound A, B, C or D | 19% |

Attaclay 15–30 is an attapulgus clay product of Minerals & Chemicals Philipp Corporation. Compound A is isopropyl 3,7,11-trimethyldodeca-2,4-dienoate, Compound B is ethyl 3,7,11-trimethyldodeca-2,4-dienoate, Compound C is t-butyl 3,7,11-trimethyldodeca-2,4-dienoate and Compound D is ethyl 3,7,11-trimethyl-thioldodeca-2,4-dienoate.

The following is an example of a water-dispersable powder formulation in accordance with the present invention:

| Hi Sil 233 | 73.5% |
|---|---|
| Igepon-T-77 | 1.0% |
| Defoamer | 0.5% |
| Compound A, B, C or D | 25.0% |

Hi Sil is a trademark of PPG Industries. Igepon-T-77 in an anionic wetting agent of GAF Corp. Defoamer is soap flakes but other defoamers can be used.

The following is an example of an emulsive formulation in accordance with the present invention:

| Solvent | 14% |
|---|---|
| Atlox 3403F | 1% |
| Atlox 3404F | 3% |
| Compound A,B,C or D | 82% |

Solvent is xylene although other solvents can be used. Atlox is trademark of Atlas Chemical Industries, Inc. The emulsive is diluted with water and applied. A deactivator such as a tertiary amine can be added to above formulation, usually in the amount of about 1% depending on shelf life desired.

As example of a concentrate which can be applied without dilution using ultra-low volume sprayer is the following:

| Solvent | 10–20% |
|---|---|
| Compound A,B,C or D | 80–90% |

Solvent can be xylene, heavy aromatic naphtha, and the like.

In the foregoing formulations, in place of compounds A,B,C or D, there can be used other compounds of the present invention of formula A described herein and combinations thereof.

EXAMPLE 41

To a solution of 1.5 g. of 3,7,11-trimethyldodeca-2,4-dienoic acid in dry benzene, under nitrogen, is added 0.8 ml of oxalyl chloride via syringe. After 2 hours, 0.8 ml of isopropylmercaptan is added and the reaction mixture left for about 60 hours. The mixture is concentrated under reduced pressure and then poured through alumina using pentane. The eluate is evaporated under reduced pressure to yield isopropyl 3,7,11-trimethylthioldodeca-2,4-dienoate which can be purified by distillation.

EXAMPLE 42

To a solution of 6.0 g of 3,7,11-trimethyldodeca-2,4-dienoic acid and 125 ml. of dry benzene, under nitrogen, is added 7 ml. of oxalyl chloride. The reaction mixture is left 1.5 hours at room temperature and heated at 60° for 0.5 hour. The solvent is evaporated off and 125 ml. of fresh dry benzene added and 4.7 g. of ethylmercaptan. The mixture is stirred for 2 hours and then refluxed gently for about 16 hours. After cooling, the mixture is poured in water and ether is added. The organic phase is separated and washed with aqueous sodium bicarbonate and brine, dried over calcium sulfate and evaporated to give ethyl 3,7,11-trimethyl-thioldodeca-2,4-dienoate which can be purified by column chromatography and distillation.

EXAMPLE 43

To a solution of 4.15 g. of 3,7,11-trimethyldodeca-2,4-dienoic acid in 100 ml. of dry benzene, under nitrogen, is added 5.1 ml. of oxalyl chloride. After 2 hours, solvent is removed under reduced pressure and 100 ml. of fresh dry benzene and 6.4 ml. of dry isobutyl alcohol is added. The reaction mixture is concentrated and the concentrate is stirred over 20 g, of activated alumina in pentane for 0.5 hr. and filtered. The filtrate is washed, dried and evaporated under reduced pressure to give isobutyl 3,7,11-trimethyldodeca-2,4-dienoate which can be purified by distillation.

EXAMPLE 44

A solution of 20 g. of potassium hydroxide granules (85%) in 80 ml. of ethanol (90%) is prepared and then hydrogen sulfide is passed into the solution with stirring and cooling until the solution is saturated and does not give an alkaline reaction with phenolphthalein. At about 10°–15°, 33.5 g. of 3,7,11-trimethyldodeca-2,4-dienoic acid is added dropwise with stirring and maintaining temperature of 10°–15°. After addition is complete, the reaction mixture is stirred for about 1 hour. Then the mixture is filtered and the filter washed with ethanol (95%). The combined filtrate and washings are evaporated under reduced pressure. Water is added to the concentrate and then extracted with benzene. The aqueous phase is acidified with cold 6N hydrochloric acid and then extracted with ether. The ether extracts are washed with cold water, dried over sodium sulfate and ether evaporated to give crude 3,7,11-trimethylthioldodeca-2,4-dienoic acid which can be purified by chromatography.

EXAMPLE 45

Following the procedure of Examples 6, 27 or 43, there is prepared the acid chloride of 3,7,11-trimethyldodeca-2,4-dienoic acid and then reacted with each of cyclopropyl alcohol, isopentyl alcohol, but-3-en-2-ol and but-3-yn-1-ol to obtain cyclopropyl 3,7,11-trimethyldodeca-2,4-dienoate,
isopentyl 3,7,11-trimethyldodeca-2,4-dienoate,
but-3'-en-2'-yl 3,7,11-trimethyldodeca-2,4-dienoate, and
but-3'-yn-1'-yl 3,7,11-trimethyldodeca-2,4-dienoate.

EXAMPLE 46

Each of allyl mercaptan, propargyl mercaptan, crotyl mercaptan, but-3-yn-1-thiol, cyclopropyl mercaptan and cyclohexyl mercaptan is reacted with 3,7,11-trimethyldodeca-2,4-dienoyl chloride according to the procedure of Example 42 to prepare - allyl 3,7,11-trimethylthioldodeca-2,4-dienoate,
propargyl 3,7,11-trimethylthioldodeca-2,4-dienoate,
crotyl 3,7,11-trimethylthioldodeca-2,4-dienoate,
but-3'-yn-1'-yl 3,7,11-trimethylthioldodeca-2,4-dienoate,
cyclopropyl 3,7,11-trimethylthioldodeca-2,4-dienoate, and
cyclohexyl 3,7,11-trimethylthioldodeca-2,4-dienoate.

By use of an atomizing device, two seeding pea plants nine to eleven days of age are sprayed until run-off is imminent. Approximately 5 ml. of spray solution are dispensed during this operation. The said spray solution is prepared by adding 1.0 ml. of an acetone solution which contains an appropriate, predetermined amount of a compound of the present invention, to 9.0 ml. of an aqueous 0.01% emulsion of the surfactant Tween 20 (polyoxyethylene (20) sorbitan monolaurate). A pair of pea plants is also sprayed with a 1 to 9 preparation of acetone in 0.01% Tween 20 to serve as spray diluent controls. The aqueous sprays on the plants are allowed to dry. Individual plants are then infested with ten third instar larvae of the pea aphid Acyrthosiphon pisum (Harris) which are 72 to 96 hours of age from time of birth. The aphids are then encaged by placing a disposable paperboard cylinder over the pot in which each sprayed and infested pea plant is maintained. The cylinder is closed at the top with fine mesh nylon screen to retain aphids which leave the plant. Encaged plant units are transferred to an environmental greenhouse maintained under constant conditions (25° C, 50% relative humidity, 16 hours per day) and held therein for a period of 6 days. During this time, the said substrate of each pea plant is watered as may be necessary. At the end of this holding period, the aphids on each plant are scored using the following system: 0 = a normal aphid. 1 = a moderatly affected aphid which exhibits characters intermediate between those of the normal adult and the fourth instar larva, and 2 = a strongly affected aphid which exhibits one or more of the following characteristics: evidence of an extra-larval instar(s), inhibited reproduction, genital pore sclerotized and cauda more larval than adult in shape. For each plant, the sum of the two products of the number of individuals in each category times the category score is divided by 20 (maximum score) to obtain the percent response. The result from the duplicate assays are average to obtain the percent response for the particular dose level applied. Two or more dose levels (stated as percent concentration) are applied for each experimental compound. The $IC_{50}$ level for each experimental compound is then determined from a semi-logarithimic plot of percent response versus the logarithm of the percent concentration. For ethyl 3,7,11-trimethylthioldodeca-2,4-dienoate; isopropyl 3,7,11-trimethyldodeca-2,4-dienoate; ethyl 3,7,11-trimethyldodeca-2,4-dienoate; isopropyl 3,7,11-trimethylthioldodeca-2,4-dienoate; n-propyl 3,7,11-trimethyldodeca-2,4-dienoate; and methyl 3,7,11-trimethylthioldodeca-2,4-dienoate. $IC_{50}$ value of less than 0.045% was obtained for each compound. Controls exhibited negligible (2% or less) response throughout the series of assays.

Each of the compounds, ethyl 3,7,11-trimethylthioldodeca-2,4-dienoate and ethyl 3,7,11-trimethyldodeca-2,4-dienoate was similarly applied to the peach aphid (Myzus persicae) and found to have an $IC_{50}$ value of less than 0.030%.

The compound, phenyl 3,7,11-trimethyldodeca-2,4-dienoate, was tested on Aedes aegypti larvae using the procedure described hereinabove and an $IC_{50}$ of less than 1.0 ppm was obtained.

What is claimed is:

1. A compound selected from those of the following formula:

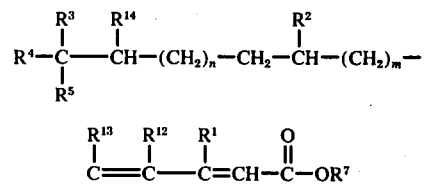

wherein,
each of $m$ and $n$ is zero or the positive integer one, two or three;
each of $R^1$ and $R^2$ is methyl or ethyl; $R^4$ is lower alkyl of one to six carbon atoms;
each of $R^3$ and $R^5$ is hydrogen, methyl or ethyl;
each of $R^{12}$, $R^{13}$ and $R^{14}$ is hydrogen or methyl; and $R^7$ is hydrogen, lower alkyl of one to six carbon atoms, lower alkenyl of three to six carbon atoms, lower alkynyl of three to six carbon atoms, cycloalkyl of three to eight carbon atoms, aryl of six to 12 carbon atoms, aralkyl of seven to 12 carbon atoms or a metal cation selected from thr group consisting of lithium, sodium, potassium, calcium, strontium, copper, manganese and zinc.

2. A compound according to claim 1 wherein $m$ is zero or one; $n$ is zero, one or two; $R^1$ is methyl; each of $R^3$ and $R^4$ is methyl or ethyl; and $R^5$ is hydrogen.

3. A compound selected from the following formula:

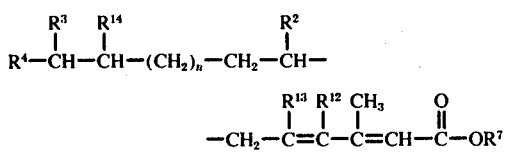

wherein, $n$ is zero or one;
each of $R^2$, $R^3$ and $R^4$ is methyl or ethyl;
each of $R^{12}$, $R^{13}$ and $R^{14}$ is hydrogen or methyl; and
$R^7$ is lower alkyl of one to six carbon atoms.

4. A compound according to claim 3 wherein each of $R^2$, $R^3$ and $R^{14}$ is methyl; each of $R^{12}$ and $R^{13}$ is hydrogen; and n is one.

5. A compound according to claim 3 wherein each of $R^{12}$, $R^{13}$ and $R^{14}$ is hydrogen.

6. A compound according to claim 5 wherein each of $R^2$ and $R^3$ is methyl and $n$ is one.

7. A compound according to claim 6 having trans(2),trans(4) or cis(2),trans(4) configuration.

8. The compound 3,7,11-trimethyldodeca-2,4-dienoic acid.

9. The trans(2),trans(4) isomer of the compound of claim 8.

10. The compound, methyl 3,7,11-trimethyldodeca-2,4-dienoate.

11. The trans(2),trans(4) isomer of the compound of claim 10.

12. The compound, ethyl 3,7,11-trimethyldodeca-2,4-dienoate.

13. The trans(2),trans(4) isomer of the compound of claim 12.

14. The compound, isopropyl 3,7,11-trimethyldodeca-2,4-dienoate.

15. The trans(2),trans(4) isomer of the compound of claim 14.

16. The compound, t-butyl 3,7,11-trimethyldodeca-2,4-dienoate.

17. The trans(2),trans(4) isomer of the compound of claim 16.

18. A compound according to claim 7 wherein $R^7$ is lower alkyl of one to four carbon atoms.

19. The compound, prop-2'-yn-1'-yl 3,7,11-trimethyldodeca-2,4-dienoate.

20. The trans(2),trans(4) isomer of the compound of claim 19.

21. The compound, prop-2'-en-1'-yl 3,7,11-trimethyldodeca-2,4-dienoate.

22. The trans(2),trans(4) isomer of the compound of claim 21.

23. The compound, 3,7,10-trimethylundeca-2,4-dienoic acid, according to claim 2.

24. The compound, ethyl 3,7,10-trimethylundeca-2,4-dienoate, according to claim 3.

25. The compound, 3,7,11-trimethyltrideca-2,4-dienoic acid, according to claim 2.

26. The compound, ethyl 3,7,11-trimethyltrideca-2,4-dienoate, according to claim 3.

27. The compound, 3,11-dimethyl-7-ethyltrideca-2,4-dienoic acid, according to claim 2.

28. The compound, ethyl 3,11-dimethyl-7-ethyltrideca-2,4-dienoate, according to claim 2.

29. The compound, 3,7,11,11-tetramethyldodeca-2,4-dienoic acid, according to claim 1.

30. The compound, ethyl 3,7,11,11-tetramethyldodeca-2,4-dienoate.

31. A compound according to claim 2 wherein each of $R^{12}$, $R^{13}$ and $R^{14}$ is hydrogen and $R^2$ is ethyl.

32. A compound according to claim 31 wherein $R^3$ is methyl and $R^4$ is ethyl.

33. A compound of the formula:

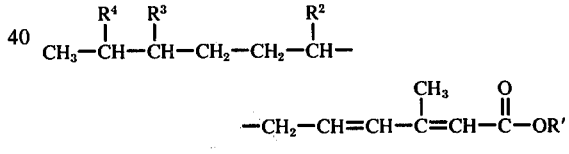

wherein, $R'$ is hydrogen, lower alkyl, lower alkenyl or lower alkynyl;
$R^2$ and $R^4$ are methyl or ethyl; and
$R^3$ is hydrogen or methyl.

* * * * *